US006495682B2

United States Patent
Cheng et al.

(10) Patent No.: US 6,495,682 B2
(45) Date of Patent: Dec. 17, 2002

(54) PROCESS FOR RECOVERING CAPROLACTAM AND STEAM

(75) Inventors: Peter W. H. Cheng, Augusta, GA (US); Jan A. J. Hendrix, Obbicht; Leonardus J. G. Raets, Elsloo, both of (NL)

(73) Assignee: DSM N.V., Heerlen (NL)

( * ) Notice: Subject to any disclaimer, the term of this patent is extended or adjusted under 35 U.S.C. 154(b) by 0 days.

(21) Appl. No.: 09/934,679

(22) Filed: Aug. 23, 2001

(65) Prior Publication Data

US 2002/0058808 A1 May 16, 2002

Related U.S. Application Data

(63) Continuation of application No. PCT/NL00/00080, filed on Feb. 9, 2001.
(60) Provisional application No. 60/122,098, filed on Feb. 26, 1999, and provisional application No. 60/122,112, filed on Feb. 26, 1999.

(51) Int. Cl.⁷ .............................................. C07D 201/16
(52) U.S. Cl. ...................................................... 540/540
(58) Field of Search ......................................... 540/540

(56) References Cited

U.S. PATENT DOCUMENTS 4,107,160 A    8/1978  Dicoi et al. ............. 260/239 A
4,605,762 A  * 8/1986  Mandoki .................... 562/483
5,681,952 A  * 10/1997 Sifniades et al. .......... 540/540
5,977,193 A  * 11/1999 Corbin et al. ............. 521/49.8
5,990,306 A  * 11/1999 Mayer et al. ............... 540/540

FOREIGN PATENT DOCUMENTS

BE         567625       5/1968
DE        1262853       2/1968
DE       19503963      11/1996
EP        0048340       3/1982
WO        9720813       6/1997

* cited by examiner

*Primary Examiner*—Bruck Kifle
(74) *Attorney, Agent, or Firm*—Pillsbury Winthrop LLP

(57) ABSTRACT

The present invention relates to a process for purifying an impure stream of caprolactam while recovering not only pure caprolactam but also medium-to-high pressure steam. Preferably, the stream of impure or crude caprolactam, which comprises at a minimum a substantial portion of water, is obtained from depolymerization of a polyamide-containing composition. The resulting purified caprolactam will have a purity greater than 90 weight percent and the recovered steam will have a temperature sufficiently high to provide a driving force for use with other equipment, for instance, heat exchange equipment.

28 Claims, 1 Drawing Sheet

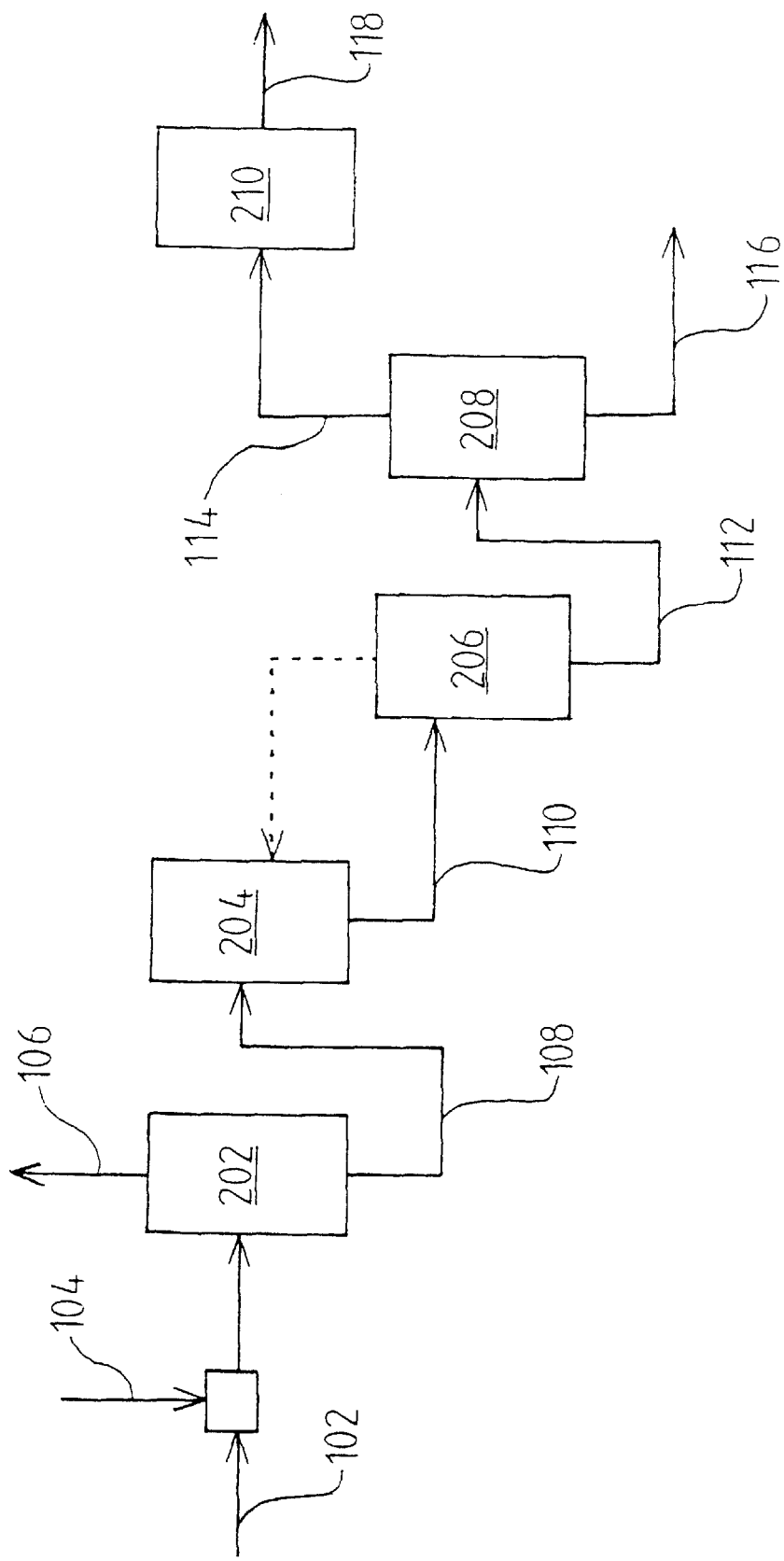

PROCESS FOR RECOVERING CAPROLACTAM AND STEAM

This is a Continuation of International Application No. PCT/NL00/00080 filed Feb. 9, 2001 which designated the U.S., and which claims the benefit of U.S. Provisional Application Nos. 60/122,098, filed Feb. 26, 1999 and 60/122,112 filed Feb. 26, 1999. Both the PCT application and the provisional applications are hereby incorporated in their entirety by reference.

FIELD OF THE INVENTION

This invention relates to an improved process for the recovery of caprolactam and medium-to-high pressure (usable) steam from a caprolactam forming process. In particular, this invention relates to an energy efficient caprolactam purification process whereby steam recovered in one part of the process may be re-used to operate equipment in other parts of the process.

BACKGROUND OF THE INVENTION

There are a number of methods known in the art for producing and purifying caprolactam. U.S. Pat. No. 2,813,858 (Joris) discusses the well known Beckman rearrangement. U.S. Pat. No. 2,813,858 also mentions methods such as hydration of adipodinitrile and reduction combined with the rearrangement of nitrocyclohexane which can also be used to prepare reaction mixtures from which lactam is recoverable, e.g., by distillation. Another source of caprolactam, as discussed in U.S. Pat. No. 5,495,014 (Fuchs et al.), involves cleaving oligomers and polymers comprised essentially of the lactam repeating unit.

U.S. Pat. No. 5,681,952 (Sifniades et al.) discusses a process for recovery of caprolactam from polycaprolactam-containing waste material. The process involves depolymerizing multi-component waste materials comprising polycaprolactam and non-polycaprolactam components to form caprolactam using superheated steam in the absence of an added catalyst. Superheated steam is fed though a distributor at the bottom of the reactor countercurrent to the flow of the melt of multi-component waste material. A vapor stream comprising caprolactam is collected at the top and condensed to obtain a condensate containing caprolactam. The caprolactam containing condensate may undergo distillation, crystallization and other conventional techniques in attempts to purify the caprolactam.

All of the processes heretofore for purifying impure caprolactam streams, whether the stream results from a caprolactam forming process or a depolymerization process, suffer from the same infirmities. The purification process is inefficient and costly to operate resulting in high energy usage, thus, raising the cost of caprolactam (which is traded as a commodity chemical). Therefore, an object of the present invention is to provide an efficient system for producing purified caprolactam.

A further object of the present invention is to provide a process for recovering purified caprolactam resulting from a depolymerization process.

Another object of the present invention is to provide a process for recovering purified caprolactam resulting from the depolymerization of polyamide-containing compositions.

Yet another object of the present invention is to provide a process for recovering purified caprolactam and medium-to-high pressure steam (usable steam).

A still further object of the present invention is to provide a caprolactam purification process whereby medium-to-high pressure steam recovered from crude caprolactam is utilized to assist the purification of the caprolactam-containing stream.

A further object of the present invention is to provide a caprolactam purification process for recovering purified caprolactam whereby the incoming caprolactam containing vapor stream is contacted with a quench fluid to minimize or prevent fouling of the distillation system with decomposition products.

SUMMARY OF THE INVENTION

The present invention relates to a process for achieving the above-noted objectives. The process involves purifying an impure stream of caprolactam while recovering not only pure caprolactam but also medium-to-high pressure steam. Preferably, the stream of impure or crude caprolactam, which comprises at a minimum a substantial portion of water, is obtained from depolymerization of a polyamide-containing composition. The resulting purified caprolactam will have a purity greater than 90 weight percent and the recovered steam will have a temperature sufficiently high to provide a driving force for use with other equipment, for instance, heat exchange equipment. One embodiment of the present invention provides a process for recovering caprolactam and usable steam comprising:

(a) providing a crude caprolactam feed stream comprising
  (i) crude caprolactam including decomposition products, and
  (ii) water and/or steam;
(b) if necessary, vaporizing the feed stream;
(c) optionally, introducing a quench fluid to remove at least a portion of the decomposition products from the vapor phase of the feed stream;
(d) distilling said vapor stream to recover medium-to-high pressure (usable) steam; and
(e) purifying said crude caprolactam to recover caprolactam.

BRIEF DESCRIPTION OF THE DRAWING

The FIGURE is a schematic flow diagram of an embodiment of a process for recovering caprolactam in accordance with the present invention.

DETAILED DESCRIPTION OF PREFERRED EMBODIMENTS

Herein certain terms are used to define elements of the present invention. Unless otherwise qualified, these terms are to be understand as having the meanings as defined below.

"crude caprolactam" refers to caprolactam which includes decomposition products but does not refer to water (or steam)

"decomposition products" refers to polyamide-containing carpet decomposition components other than caprolactam including: nylon and nylon derivatives, such as 6-aminocaproic acid, caprolactam dimer, linear oligomers of caprolactam, cyclic oligomers of caprolactam, N-methylcaprolactam, N-ethylcaprolactam, hexenoic acid, cyclohexylamine, 1,6-hexanediamine, acetic acid and the like; and non-nylon derivatives such as styrene-butadiene rubber derivatives, polypropylene derivatives, polyethylene terephthalate fiber derivatives and the like including 1,3- diphenylpropane, styrene dimer, styrene-butadiene oligomers, aliphatic alcohols (including: 1-decanol, 1-dodecanol, glycols, in particular ethylene glycol, and the like); acids, in particular, carboxylic acids with 4 to 16 carbon atoms per molecule including benzoic and terephthalic acids; amides with 4 to 16 carbon atoms per molecule and the like which may exist, for instance, in the crude caprolactam feed stream as viscous/solid particles, liquids, vapors, gases and/or other entrained substances.

"polyamide-containing composition" refers to materials comprising at least 15% polyamide. Typically, these articles include pre-consumer and/or post-consumer rework and/or scrap materials. Preferably, polyamide-containing composition includes polyamide fiber containing articles including polyamide-containing carpet. If the polyamide-containing article comprises poly(hexamethylene diamine adipate) ("nylon 66") fibers in addition to polycaprolactam ("nylon 6") fibers, the nylon 66 depolymerization products may condense in addition to the nylon 6 depolymerization products. If the polyamide-containing article comprises polyethylene terephthalate fibers in addition to nylon 6 fibers, the depolymerization step may produce benzoic and terephthalic acids as well as ethylene glycol which may volatilize with the lactam and water. Terephthalic acid is insoluble in water and is preferably removed to prevent difficulty during the subsequent caprolactam purification.

"polyamide-containing carpet" refers to carpet resulting from scrap generated during carpet manufacturing, carpet recycling, carpet installation, or removal of installed carpet and comprising face fiber, preferably nylon face fiber, that is adhered to a support material such as jute or polypropylene backing, latex (such as a styrene-butadiene rubber (SBR)), and a variety of inorganic materials such as calcium carbonate, clay, or hydrated alumina fillers.

"pressure" refers to absolute pressure.

"purified caprolactam" refers to caprolactam having a purity greater than 90 weight percent, preferably, a purity of greater than 95 weight percent.

"usable steam" which is also referred to as "medium-to-high pressure steam" refers to steam having sufficiently high temperature to be suitable, for instance, as a heat source for heat exchange equipment.

A) Depolymerization

A polyamide-containing composition is preferably fed to the reactor as a melt. This feeding may be achieved by using an extruder, gear pump, or other means known in the art. For instance, the polyamide-containing composition may include carpet, as a polyamide-containing article, processed to a size to be melted efficiently by, for example, cutting or shredding the carpet, and feeding to an extruder, as described in U.S. Pat. No. 5,681,952 which is hereby incorporated by reference in its entirety.

The polyamide-containing feed stream will typically comprise between 30 to 80 wt. % polyamide, preferably, between 35 to 65 wt. % polyamide. The polyamide-containing article is depolymerized to form caprolactam. Caprolactam may be formed by contacting the polyamide-containing article with water or steam. In the depolymerization process, decomposition products may be formed including linear oligomers of caprolactam, and cyclic oligomers of caprolactam. In addition, the feed materials (polyamide-containing articles) may also contain other materials, for example, backing materials, fibers, impurities, and the like. Thus, when caprolactam is recovered from the depolymerization process, the caprolactam will be in a crude form where it contains some quantity of decomposition products and other materials.

The depolymerization is preferably conducted at a temperature of at least 250° C. but not higher than 400° C. Although temperatures below 250° C. may be used, the depolymerization at these conditions may be too slow. Generally, the rate of caprolactam formation increases with increasing temperature. Temperatures no greater than about 400° C. are preferred because at temperatures above 400° C. side reactions of nylon 6 and reactions of the non-nylon 6 components will be more competitive which will result in a stream having more impurities. The preferred temperature range is about 280° C. to about 350° C., more preferably about 300° C. to about 340° C. The depolymerization can be achieved either with steam, preferably superheated steam, or water maintained under sufficient pressure to accommodate the above-noted temperatures. If water maintained at a high pressure is employed to depolymerize the polyamide, the resulting crude caprolactam-containing feed stream (also referred to herein as the "crude caprolactam feed stream") will be vaporized, preferably by allowing the pressure to drop, when entering the purification process.

Depending on the amount of water or steam required for depolymerization, the resulting crude caprolactam-containing feed stream may have a ratio of 1:1 to 50:1, preferably 2:1 to 10:1, more preferably 5:1 to 10:1, kilograms of steam/water per kilogram of crude caprolactam. Preferably, the crude caprolactam feed stream will have a pressure of 0.2–1.5 MPa, more preferably 0.9–1.4 MPa., or most preferably 1.0–1.3 MPa. When the crude caprolactam feed stream results from a water depolymerization, the feed stream may have a pressure as high as 12 MPa, preferably between 7–10 MPa. The crude caprolactam feed stream will typically have an energy value of at least $1.8 \times 10^6$ J/kg, more preferably, between about $2.1 \times 10^6$ to $3.2 \times 10^6$ J/kg.

B) Quenching

Prior to distilling the crude caprolactam, the crude caprolactam vapor feed stream (referring to a crude caprolactam feed stream resulting from steam depolymerization, a crude caprolactam feed stream that becomes vaporized, e.g., a vaporized feed stream resulting form water depolymerization, and/or a crude caprolactam feed stream that remains substantially vapor after contact with the quench fluid) may optionally be contacted with a quenching fluid to reduce or eliminate the decomposition products that may be carried or are entrained in the vapor phase of the crude caprolactam vapor stream. If the vapor stream is allowed to enter a distillation process without reducing, or preferably eliminating, these decomposition products in the vapor portion of the feed stream, these decomposition products may foul or build-up (e.g., by condensing) on the distillation equipment it contacts. In particular, as the crude caprolactam vapor stream velocity is slowed down in the distillation process and/or the decomposition products impact other materials (including equipment) and/or are cooled down, the components may coagulate, (partially or completely) solidify, or otherwise settle on the distillation equipment. This results in deposits or layers of these decomposition products forming on the packing, trays, and/or other contacted portions of the distillation equipment which causes the distillation process to become inefficient and may ultimately lead to blockage that results in more frequent operation shutdowns for equipment cleaning and/or replacement.

The quenching fluid can be brought into contact with the crude caprolactam feed stream in a variety of ways. For instance, the quenching stream can be injected or sprayed into the crude caprolactam vapor stream either at the point of entry to the distillation system or at a point upstream thereto. Preferably, the quench water will be introduced into the vapor stream in an area proximate with the entrance of the crude caprolactam vapor feed stream into the distillation system. Preferably, the quench fluid will be sprayed into the midst of the crude caprolactam vapor feed stream so as to knock-out and/or partially or wholly condense decomposition product components that are in the vapor phase of the feed stream.

Preferably, the quench fluid will be introduced so that the decomposition products will be eliminated from the vapor phase of the feed stream and carried into the distillation system in a manner causing them to pass or drop to the bottoms of the distillation system. For example, a spray nozzle may be positioned proximate with the center of the passing crude caprolactam vapor feed stream to inject the quench fluid in all directions, including transverse and/or parallel, with the travel direction of the feed stream. Although the spray nozzle may be movable or continuously moving, it is preferably fixedly positioned to direct the quench fluid in a direction concurrent with the feed stream.

The quench fluid may be any fluid suitable for this purpose including water, wastewater, condensed steam, recycled crude-caprolactam containing fluids and/or the like. Preferably, the quench fluid will include fluids recycled from other portion of the purification process which may include reflux water from the distillation column, or any other condensed overhead streams or bottom streams from the purification process. The advantage of recycling a condensed stream or reflux stream from the purification process for use as the quench fluid is that it reduces the overall quantity of water used and expelled by the process and, moreover, these recycled fluids may contain caprolactam that may be recovered.

The temperature of the quench fluid can be any temperature above the freezing point of the quenching fluid up to the temperature of the crude caprolactam vapor stream. Preferably, the quench fluid will have a temperature between 0° C. to 200° C., more preferably, between 25° C. and 100° C. and will comprise mostly water, preferably greater than 70 wt. % water. The amount of quench fluid employed will depend both on the temperatures of the quench fluid and the vapor stream, and the quantity of the vapor to be condensed. As the decomposition products make up a very small portion of the vapor stream, preferably, in the order of less than 0.02 wt. % (relative to the total weight of the vapor stream), typically, the ratio of quench fluid to crude caprolactam vapor stream (prior to the introduction of the quench fluid), on weight-by-weight basis, will not exceed 1:1. More preferably, the quench fluid will be introduced on a weight basis at a ratio between 0.001 to 0.5, in particular, between 0.001 to 0.2, relative to the crude caprolactam vapor feed stream. Preferably, the quench fluid will eliminate greater than 50 wt. %, and more preferably 75 wt. %, relative to the total weight of the decomposition products in the vapor feed stream prior to contact with the quench fluid, from the vapor phase of the feed stream.

C) Recovering Usable Steam

A crude caprolactam containing vapor stream may be fed directly to the purification process. Preferably, the crude caprolactam containing stream results from a depolymerization reaction and, if depolymerized by high pressure water, is allowed to vaporize and, if necessary, partially condense before being fed to the distillation system. Any suitable distillation system may be used for this purpose including a single or multi-stage or multi-column distillation system.

As crude caprolactam is distilled from the vapor stream in a distillation system (also referred to herein as the "first distillation system" and the "high-pressure distillation system") maintained at an elevated pressure, usable steam is recovered from the overhead and the condensed phase, typically exiting the bottom, comprises a higher percentage of crude caprolactam. The bottom product will typically comprise between 55 to 90 wt. % crude caprolactam, preferably, between 65 to 75 wt. % crude caprolactam.

The high-pressure distillation system is operated at a pressure level below the pressure of the incoming vapor stream but at a pressure sufficiently high so that the steam recovered has a temperature sufficiently high enough to be used, for example, as the heat providing stream for heat exchange equipment. Since substantial amounts of useable steam can be recovered from this process, the steam can usefully be used to raise the temperature of, for example, an exchange fluid to within a couple of degrees of the temperature at which the steam is initially recovered. More typically, the steam will be useful for situations wherein the steam is at least 5° C. higher, preferably, 10° C. higher than the material being heated. Typically, the distillation is performed at a pressure of from 0.2 to 1.0 MPa, preferably, 0.3 to 0.7 MPa, and more preferably, 0.40–0.50 MPa. Preferably, the usable steam will have from $2.1 \times 10^6$ to $3.2 \times 10^6$ J/kg of energy, and more preferably $2.6 \times 10^6$ to $2.8 \times 10^6$ J/kg of energy.

Referring to the FIGURE, the vapor stream 102 is (optionally) contacted with a quench fluid stream 104 introduced upstream of the distillation system 202. In the distillation system, the vapor stream is separated into a usable steam stream 106 and a condensed or liquid stream comprising crude caprolactam exits as the bottom stream 108. The recovered usable steam 106 may be used to provide heat energy to other equipment in the purification process.

D) Purification

The bottom product from the steam recovery step is further purified to recover pure caprolactam. Any suitable process for purifying the caprolactam may be used including additional distillation steps, crystallization, and/or combination thereof.

i) De-watering

In the de-watering process, substantially all water remaining in the crude caprolactam stream 108 is removed. Preferably, this is achieved by distilling. For example, referring to the FIGURE, the bottom product stream 108 is fed to a second distillation system 204. The second distillation system 204 may include multi-stages. These multi-stages may include any suitable distillation equipment such as multiple vessels, multiple distillation columns, and/or at least one distillation column containing multiple trays. Typically, at least one stage in this distillation system will operate at atmospheric pressure or below to assure that substantially all the water is removed from the crude caprolactam.

Preferably, this second distillation or dewatering is accomplished in a multi-stage fashion such that further decomposition of the crude caprolactam does not occur. More preferably, distillation is performed in a multi-column system in a manner so that the conditions in the columns are, relative to the amount of water remaining in the crude caprolactam stream, below the conditions (in particular, temperature and/or residence time) where oligomerization may become a concern. For instance, when the crude caprolactam stream exiting a given distillation column is below 30 wt. % water, the time the crude caprolactam is exposed to temperatures above 140° C. should be less than 30 minutes, more preferably less than 10 minutes. Of course the higher the temperature, the shorter the time period before oligomerization becomes a concern. If the columns are operated below 140° C., preferably below 100° C., the residence time becomes less of a concern. In particular, as the wt. % of water becomes less, for instance 15 wt. % or less, the temperature should preferably not exceed 135° C. for extended periods. Similarly, as the wt. % of water drops below 10 wt. % or less, it is preferred that the temperature is maintained below 132° C.

Once the water content in the crude caprolactam stream falls below 15 wt. % water, more preferably, below 10 wt. % water, the remaining water can be removed by further distillation and/or flashed off using any suitable means including a knock-out drum.

In the FIGURE, the crude caprolactam stream 110 exits the second distillation system 204 and is preferably fed to a knock-out drum 206 operating at atmospheric pressure or under vacuum. Preferably, the knock-out drum operates at 15 kPa or lower. Substantially all remaining water is removed in the knock-out drum 206 and the exiting crude caprolactam stream 112 comprises less than 2 wt. % water, preferably less than 1 wt. %. Preferably, the overhead stream from the knock out drum may be recovered and recycled to prevent caprolactam loss.

The usable steam 106, recovered from the first high pressure distillation system 202, may be used to operate reboilers for the second multistage distillation system, or other distillation, evaporation, or heating systems. For example, the usable steam 106 from the first distillation system may be used to heat reboilers for the second distillation system. Preferably, the first distillation system will be operated at a pressure such that the usable steam 106 recovered therefrom will have a temperature at least 10° C. more than, more preferably at least 15° C. more than, the temperature at which the second distillation column operates.

ii) Lactam Evaporation

Pure caprolactam may be recovered from the crude caprolactam stream 112 by any suitable means known for achieving purification including evaporation. For instance, the crude caprolactam may be fed to a lactam evaporation vessel 208 at a temperature and pressure so that when the pressure is lowered (released) in the vessel a major portion of the caprolactam will vaporize 114. Meanwhile, the decomposition products and other impurities concentrate along with a minor portion of the caprolactam in an effluent stream 116. Preferably, the conditions in the lactam evaporation vessel are designed so that a suitable amount of caprolactam, which has a lower viscosity than the average viscosity of the decomposition products, remains in the effluent stream 116 to allow the effluent (or residue) to be easily removed from the lactam evaporation vessel. Preferably, the lactam evaporation vessel is operated such that the effluent is flowable at the operating conditions.

Depending on the specific composition of the crude caprolactam, the lactam evaporation vessel 208 may be operated at a pressure of less than about 1,067 Pa, preferably between 150 and 800 Pa, and a temperature from about 110° C. to about 150° C., more preferably between 118° C. to 130° C., as measured in the liquid phase, so as to form a caprolactam overhead stream 114 comprising at least 70 wt. % and no more than 85 wt. % of the caprolactam in the crude caprolactam feed. Preferably, the lactam evaporation vessel 208 is operated so that 75 wt. % to 80 wt. % of the caprolactam in the crude caprolactam feed stream is recovered in the overhead stream and 25 to 20 wt. % of the total caprolactam remains in the effluent stream 116 with the product impurities. More preferably, the lactam evaporation vessel 208 is operated so that 75–78 wt. % of the caprolactam in the crude caprolactam feed stream is recovered in the overhead stream 114 and 22–25 wt. % of the total caprolactam remains in the effluent stream 116. The effluent may comprise caprolactam, oligomers of caprolactam, 6-aminocaproic acid, N-methylcaprolactam, N-ethylcaprolactam, hexanoic acid, hexenoic acid, 1-decanol as well as other impurities.

The resulting caprolactam overhead stream 114 is then fed to a purification system 210 (e.g., distillation, crystallization or the like). From the bottom of the lactam evaporation vessel 208, the concentrated crude caprolactam effluent 116 is processed to separate the caprolactam from the oligomers and 6-aminocaproic acid. This can be done by any suitable means such as distillation and/or stripping or the like.

The caprolactam overhead stream 114 may be further purified by any conventional purification system 210. The method generally taught by U.S. Pat. No. 2,813,858, which is hereby incorporated in its entirety by reference, may also be used. The recovered product 118 may then be washed with pure lactam or a lactam solution. The resulting caprolactam is at least 95% pure, preferably 98% pure and more preferably 99% pure. If necessary, the purification process may be repeated.

EXAMPLES

While the invention has been described in detail and with reference to specific embodiments thereof, it will be apparent to those of ordinary skill in the art that various changes and modifications can be made therein without departing from the spirit and scope thereof.

The invention will be further illustrated by the following examples which are intended to be illustrative, but not limiting.

Comparative Example I

Crude caprolactam obtained from polyamide containing carpet was dewatered from 35 wt. % down to approximately 0.1 wt. % water at a bottoms temperature of 170° C. and a top pressure of 0.005 MPa. The oligomer content increased from 0.48% to 0.97% (based on caprolactam). During subsequent evaporation of caprolactam, solids were deposited and the bottoms became viscous.

Example 1

Crude caprolactam (35% water) obtained from polyamide containing carpet was kept at 155° C. and autogeneous pressure for 1 hour. The oligomer content did not increase. The crude was dewatered at a bottoms temperature of 70° C. and a pressure of 0.015 MPa. When the water content of the crude reached 10 wt. %, the remaining water was evaporated at a bottoms temperature of 130° C. Afterwards, pure caprolactam was collected overhead by evaporating 74 wt. % of the crude caprolactam at 125° C. and 300 Pa. During all stages the bottom stream remained clear and processable (low viscosity).

Comparative Examples II (A&B) and Examples 2 (A&B)

A series of experiments were conducted on dewatered crude caprolactam obtained from "depolymerized polyamide containing carpet". The dewatered crude caprolactam was evaporated at a bottom temperatures ranging between 131° C. and 133° C., at times the temperature briefly extending as high as 137° C. The maximum pressure did not exceed 600 Pa. The ratios of the caprolactam in the overhead relative to that remaining in the residue and the observed properties of the residue are presented in Table 1.

TABLE 1

| Experiment | Overhead/Residue | Residue Properties |
|---|---|---|
| Comparative Example IIA | 89/11 | Strong fouling, bottom viscous, pump problems |
| Comparative Example IIB | 85/15 | Strong fouling, bottom viscous |
| Example 2A | 81/19 | Low fouling |
| Example 2B | 71/29 | Low fouling, significantly less bottoms viscosity |

Comparative Example III

During a 4 month period, a series of pilot plant trials were performed during which vapor from a depolymerization process was fed to a reflux column containing 10 trays and no reboiler. A typical vapor feed rate was 140 kg/hr, containing 15 wt. % caprolactam, 1.5 wt. % impurities, and the balance water, at 1 bar and 320° C. On average once a week the column bottom was inspected. On every occasion a polymer-like deposition was found sticking to the bottom tray and the column wall. This had to be removed to prevent column operating problems.

Example 3

During a 2 month period, a series of pilot plant trials were performed during which a vapor stream as in Comparative Example III was contacted with a quench fluid. The quench fluid consisted of a bottoms fluid from the reflux column which had a 70 wt. % caprolactam and was fed at a rate of 4 dm³/min. On average once a week the column bottom was inspected. During the normal reactor operation, no significant deposition of polymer-like material was detected on the trays or the column wall.

What is claimed is:

1. A process for recovering caprolactam and usable steam comprising:
   (a) depolymerizing a polyamide-containing composition in the presence of water or steam to obtain a vapor stream comprising:
      (i) crude caprolactam, and
      (ii) steam;
   (b) recovering usable steam from said vapor stream; and
   (c) purifying said crude caprolactam to obtain caprolactam.

2. The process according to claim 1, wherein said polyamide-containing composition includes carpet.

3. The process according to claim 1, wherein said vapor stream contains a ratio of 1:1 to 50:1 kilograms of steam per kilogram of crude caprolactam.

4. The process according to claim 1, wherein said vapor stream is at a temperature of 250° C. to 400° C.

5. The process according to claim 1, wherein said vapor stream is at a pressure of 0.2 to 1.5 MPa.

6. The process according to claim 1, wherein said usable steam is at a pressure greater than 0.2 MPa.

7. The process according to claim 1, wherein the recovery of said usable steam is performed by a distillation column operated at a pressure from about 0.2 to 1.0 MPa.

8. The process according to claim 1, wherein said usable steam is used in purifying said crude caprolactam.

9. The process according to claim 1, wherein said usable steam has $2.1 \times 10^6$ to $3.2 \times 10^6$ J/kg of energy.

10. The process according to claim 7, wherein a bottom stream of the distillation column comprises water and crude caprolactam.

11. The process according to claim 10, further comprising removing substantially all of said water from said bottom stream to form a concentrated crude caprolactam stream.

12. The process according to claim 11, wherein said water is removed through a multistage distillation.

13. The process according to claim 12, wherein said water is further removed by a knock-out drum.

14. The process according to claim 11, wherein said distillation occurs at a temperature below the temperature at which oligomers are formed.

15. The process according to claim 14, wherein said distillation occurs at a temperature below 140° C.

16. The process according to claim 11, wherein said distillation has a residence time of less than 30 minutes.

17. The process according to claim 12, wherein said multistage distillation is performed using said usable steam.

18. The process according to claim 1, wherein said caprolactam is at least 90% pure.

19. A process for recovering caprolactam from a vapor feed stream comprising crude caprolactam and steam, wherein said crude caprolactam comprises caprolactam and decomposition products;
   said process comprising:
   (a) introducing a quench fluid to remove at least a portion of the decomposition products from the vapor phase of the feed stream.;
   (b) distilling said vapor feed stream to reduce the water content; and
   (c) recovering purified caprolactam.

20. The process according to claim 19, wherein said quench fluid is introduced at a temperature lower than the temperature of the vapor feed stream.

21. The process according to claim 19, wherein said quench fluid includes reflux from a distillation column.

22. The process according to claim 19, wherein substantially all of the decomposition products are removed through a bottom stream of a distillation column.

23. A process for recovering pure caprolactam comprising:
   (a) depolymerizing a polyamide-containing composition in the presence of water or steam to obtain a vapor stream comprising:
      (i) crude caprolactam, and
      (ii) steam; and
   (b) purifying said crude caprolactam stream by exposing said crude caprolactam to conditions such that pure caprolactam is recovered while sufficient amounts of caprolactam remain in a liquid residue such that the residue is flowable.

24. The process according to claim 23, wherein said purification occurs at a pressure between 150 Pa and 800 Pa.

25. The process according to claim 23, wherein said purification occurs at a temperature between 118° C. and 130° C. as measured in the liquid phase.

26. The process according to claim 23, wherein said purification comprises evaporating a portion of the caprolactam present in said crude caprolactam.

27. The process according to claim 26, wherein said evaporation portion is between 75–80 wt. %.

28. The process according to claim 23, wherein said purification occurs in a lactam evaporation vessel, said evaporation vessel having a feed stream, and overhead stream, and a bottom stream, wherein said overhead stream comprises 75–78 wt. % of the feed stream, and said bottom stream comprises 22–25 wt. % of the feed stream.

* * * * *

UNITED STATES PATENT AND TRADEMARK OFFICE
CERTIFICATE OF CORRECTION

PATENT NO.    : 6,495,682 B2                                                Page 1 of 1
DATED         : December 17, 2002
INVENTOR(S)   : Cheng et al.

It is certified that error appears in the above-identified patent and that said Letters Patent is hereby corrected as shown below:

<u>Title page,</u>
Item [63], Related U.S. Application Data, please correct the filing date of the PCT application to read:
-- Continuation of application No. PCT/NL00/00080, filed on Feb. 9, 2000. --

Signed and Sealed this

Eighth Day of April, 2003

JAMES E. ROGAN
*Director of the United States Patent and Trademark Office*